United States Patent [19]

Knuth

[11] Patent Number: 5,484,445
[45] Date of Patent: Jan. 16, 1996

[54] SACRAL LEAD ANCHORING SYSTEM

[75] Inventor: Henricus M. Knuth, Kerkrade, Netherlands

[73] Assignee: Medtronic, Inc., Minneapolis, Minn.

[21] Appl. No.: 135,108

[22] Filed: Oct. 12, 1993

[51] Int. Cl.⁶ ............................................. A61N 1/00
[52] U.S. Cl. .................. 606/129; 606/69; 607/41; 607/118; 607/149; 607/152
[58] Field of Search ................... 606/53, 60, 61, 606/62, 69, 70, 71, 76, 129, 151, 232, 228; 604/174, 175; 607/36, 39, 40, 41, 43, 57, 149, 152, 115–118, 138

[56] References Cited

U.S. PATENT DOCUMENTS

| | | | |
|---|---|---|---|
| 3,577,837 | 5/1971 | Bader | 606/69 |
| 3,683,911 | 8/1972 | McCormick | 128/214 R |
| 4,217,664 | 8/1980 | Faso | 604/175 |
| 4,219,027 | 8/1980 | Lund | 128/642 |
| 4,549,545 | 10/1985 | Levy | 606/228 |
| 4,569,351 | 2/1986 | Tang | 128/419 |
| 4,577,534 | 3/1986 | Rayne | 81/484 |
| 4,607,639 | 8/1986 | Tanagho et al. | 128/419 |
| 4,645,492 | 2/1987 | Weeks | 604/174 |
| 4,739,764 | 4/1988 | Lue et al. | 128/419 |
| 4,773,402 | 9/1988 | Asher et al. | 128/69 |
| 4,886,501 | 12/1989 | Johnston et al. | 604/175 |
| 4,943,292 | 7/1990 | Foux | 606/70 |
| 5,127,912 | 7/1992 | Ray et al. | 606/61 |
| 5,269,810 | 12/1993 | Hull et al. | 128/642 |

*Primary Examiner*—Stephen C. Pellegrino
*Assistant Examiner*—Jeffery A. Schmidt
*Attorney, Agent, or Firm*—Michael J. Jaro; Harold R. Patton

[57] ABSTRACT

A simple and reliable system for anchoring a lead to the sacrum. The system provides a pliant slid-on anchoring sleeve featuring a suturing groove for lead fixation and a base having screw tabs for anchoring the sleeve and thus the lead to the sacrum. The base is reinforced, preferably through a mesh, to prevent tearing caused by screw forces. In addition an elongate washer may be further used in conjunction with screws to anchor the system to bone.

21 Claims, 3 Drawing Sheets

SACRAL LEAD ANCHORING SYSTEM

FIELD OF THE INVENTION

This invention relates to an anchoring system and specifically to a system for anchoring an electrical lead to the sacrum.

BACKGROUND OF THE INVENTION

The present invention relates to the art of selective nerve stimulation. The invention finds particular application in conjunction with urination control and will be described with particular reference thereto. It is to be appreciated that the invention is also applicable to control other aspects of the nervous system, such as for fecal incontinence, penile erection, and others.

The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum.

The sacrum, generally speaking, is a large, triangular bone situated at the lower part of the vertebral column, and at the upper and back part of the pelvic cavity. The spinal canal runs throughout the greater part of this bone. It lodges the sacral nerves, and is perforated by the anterior and posterior sacral foramina through which these pass out.

Several systems of stimulating sacral nerves exist. For example, U.S. Pat. No. 4,607,639 to Tanagho et al. entitled "Method and System for Controlling Bladder Evacuation" incorporated herein by reference, and the related U.S. Pat. No. 4,739,764 to Lue et al. entitled "Method for Stimulating Pelvic Floor Muscles for Regulating Pelvic Viscera" also incorporated herein by reference, disclose implanting an electrode on at least one nerve controlling the bladder. In one embodiment the electrode is percutaneously implanted through the dorsum and the sacral foramen of the sacral segment S3 for purposes of selectively stimulating the S3 sacral nerve. The electrode is positioned using a hollow spinal needle through a foramen (a singular foramina) in the sacrum. The electrode is secured by suturing the lead body in place. U.S. Pat. No. 4,569,351 to Tang entitled "Apparatus and Method for Stimulating Micturition and Certain Muscles in Paraplegic Mammals" incorporated herein by reference, discloses use of electrodes positioned within the sacrum to control bladder function.

Typically electrical stimulation of the nerves within the sacrum is accomplished by positioning a lead having at least one electrode at its distal end through a foramen of the sacrum and proximate the nerve. Of course to reliably exercise nerve and thus bladder or bowel control the electrode must remain anchored in its intended location.

Movement of the lead, whether over time from suture release, or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation which, in turn, requires consistent presence of the electrode portion of the lead proximate the nerve.

Past leads have been anchored through the use of one or more suture sleeves. Specifically the suture sleeves were tied or sutured about the lead, as is well know in the art, and further sutured to the tissue proximate the sacrum.

This type of anchoring system, however, has several drawbacks. First the sutures may only be tied to the tissue surrounding the sacrum. That tissue, however, is relatively weak and only one or two sutures may be placed through it. Even then the fixation of the lead is less than wholly reliable. In addition, while the suture sleeve is being positioned and sutured to the tissue, the lead may move from the optimal site.

The U.S. Pat. No. 4,569,351 to Tang, discussed above, featured electrodes positioned and fixed to the sacrum through use of a holder. The holder features a hole through which the electrodes extend. Electrode access to the sacral nerves is achieved by the drilling of holes. The holder is rigid, preferably made from a non-conductive, molded material, such as methyl-methacrylate. The holder is fixed to the sacrum through a set of screws. This holder design, however, is less than wholly satisfactory. For example lead implantation is not satisfactorily provided. Specifically, because electrodes extend a fixed length from the holder, once they have been tailored to length and the holder positioned and mounted to the sacrum, the electrodes cannot be further adjusted. In addition, the rigidity of the holder presents several drawbacks. First, it requires the removal of any bony protrusions in order to provide a substantially flat surface against which the holder is to abut. Second, the rigid holder as well as the upstanding lead position tends to concentrate any bending forces to the section of the lead near the holder. As may be appreciated, concentrated bending forces and the resultant increased strain to the lead may result in lead fracture.

SUMMARY OF THE INVENTION

It is thus an object of the present invention to provide a simple and reliable system to anchor a lead to the sacrum.

It is a further object of the present invention to provide a simple and reliable system to anchor a lead to the sacrum which will permit the electrode to be properly located and remain positioned while the anchor is installed.

It is a further object of the present invention to provide a simple and reliable system to anchor a lead to the sacrum which permit the anchoring system to be installed without requiring the removal of any bony protrusions.

It is a further object of the present invention to provide a simple and reliable system to anchor a lead to the sacrum which will provide an adequate dissipation of bending forces and strain in the section of the lead near the anchoring system.

These and other objects are met by the present invention which provides a simple and reliable system for anchoring a lead to the sacrum. The system provides a pliant slid-on anchoring sleeve featuring a suturing groove for lead fixation and a base having screw tabs for anchoring the sleeve and thus the lead to the sacrum. The base is reinforced, preferably through a mesh, to prevent tearing caused by screw forces. In addition an elongate washer may be further used in conjunction with screws to anchor the system to bone. Such an anchoring system is relatively easily installed, provides strain relief to the section of the lead near the anchor and permits adjustment of the electrode near the nerve after the anchor is installed.

DETAILED DESCRIPTION OF THE INVENTION

Figure 1:
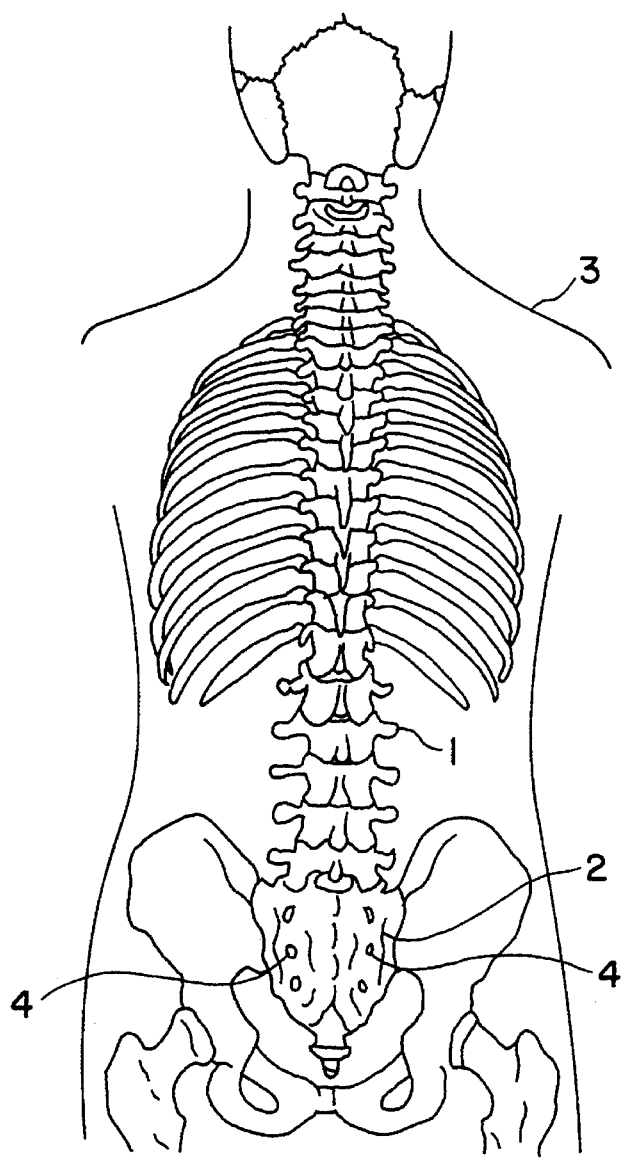
FIG. 1 is a posterior view of the spinal column showing the location of the sacrum relative to an outline of a body.

FIG. 1 is a posterior view of the spinal column 1 showing the location of the sacrum 2 relative to an outline of a body 3. As seen, the sacrum 2 has a series of holes, known as foramina 4, therethrough. Each foramen 4 (as they are referred to in the singular) provides access to the sacral ventral nerves (not shown.) As discussed above electrical stimulation of these nerves is useful to effect control of an organ, such as a bladder (not shown.)

Figure 2:
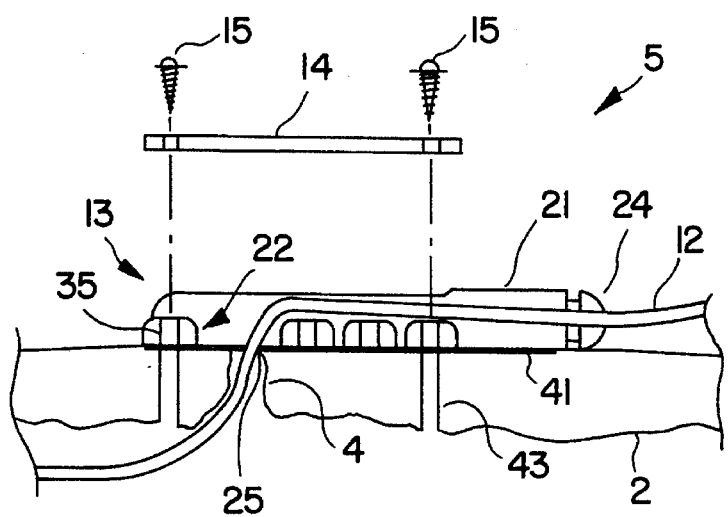
FIG. 2 is a plan side view showing an anchoring system of the present invention shown anchoring a lead to the sacrum.

FIG. 2 shows an anchoring system 5 according to the present invention mounted to sacrum 2 and thus anchoring lead 12. As seen anchoring system 5 comprises body member 13 mounted to sacrum 2 through elongate washer 14 and screws 15. Body member 13 is preferably constructed from a pliant biocompatible material, such as silicone or polyurethane. Body member 13 has two sections sleeve 21 and base 22.

Sleeve 21 has lead lumen 23 extending from proximal end 24 to opening 25 in bottom side 31. Lead lumen 23 is dimensioned to have lead 12 extend therethrough. Located along inner surface 32 of lead lumen 23 proximate suture groove 33 are lead fixation tabs 34. Tabs 34 are dimensioned to frictionally engage lead 12 within lead lumen 23 when a suture (not shown) is positioned with and tightened around suture groove 33, as is well known in the art. Although one suture groove 33 is shown, more than one may be provided to secure the lead if necessary.

Base 22 has mounting holes 35 extending therethrough. Mounted to bottom side 31 of base 22, in the preferred embodiment, is reinforcing member 41. Reinforcing member 41 provides protection from tearing of body member 13 by screws 15 in mounting holes 35 and is preferably a nylon mesh fixed with a biocompatible adhesive to bottom surface 31 of body member 13. Reinforcing member 41 may further be constructed in any other fashion or from various other materials to provide strain relief to mounting holes 35, such as being molded directly within body member 13.

As seen in FIG. 2 body member 13, and thus lead 12 extending therethrough, is anchored to sacrum 2 by screws 15 and elongate washer 14. Elongate washer 14 functions as a stress distribution member to distribute the stress exerted from screws 15 through base 22 and not only proximate mounting holes 35. Thus elongate washer 14 provides further protection, along with reinforcing member 41, from tearing of the pliant material of body member 13. Although elongate washer is shown as a separate component of the anchoring system of the present invention, it may also be molded directly within or to body member 13, and in particular within or to base 22.

Figure 3:
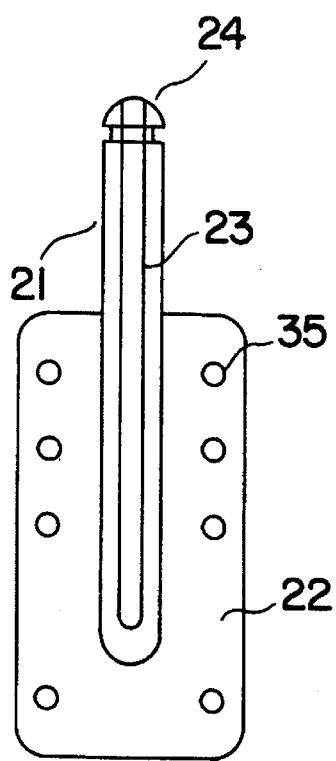
FIG. 3 is a plan top view of an anchoring system of the present invention.
Figure 4:
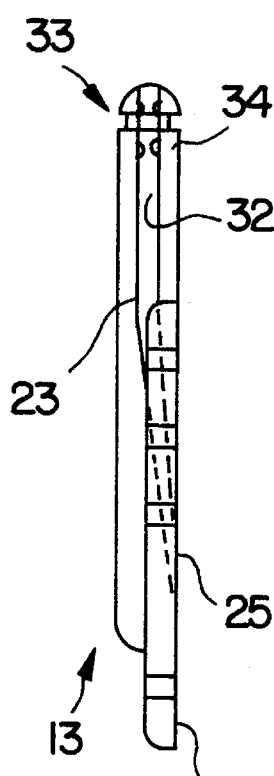
FIG. 4 is a plan side view of an anchoring system of the present invention.

FIGS. 3–11 show alternate embodiments of the present anchoring system 5. Although not shown in use with elongate washer 14, screws 15, or reinforcing member 41 each of these embodiments are mounted in substantially the same manner as previously discussed. FIGS. 3 and 4 depict an alternate embodiment in which base 22 is a continuous sheet of material. Lead lumen 23, moreover, gradually bends towards bottom 31 of body member 13.

Figure 5:
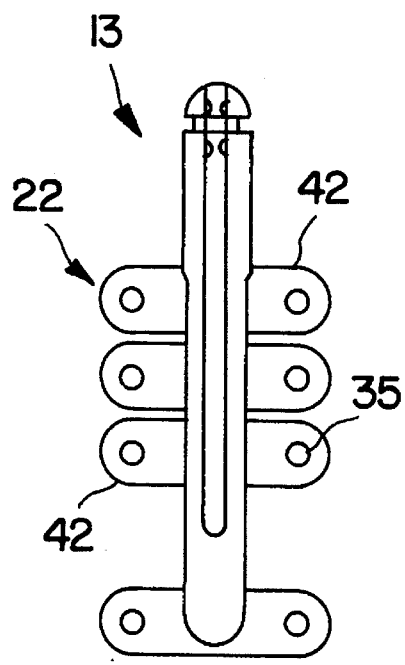
FIG. 5 is a plan top view of an alternate embodiment of an anchoring system of the present invention.
Figure 6:
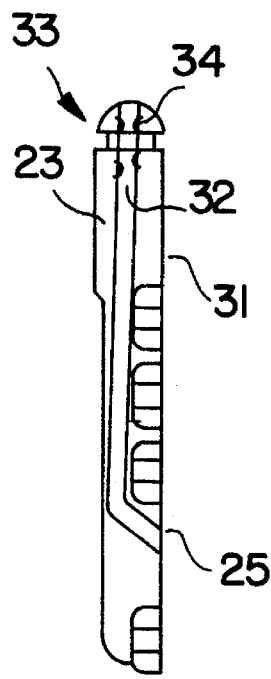
FIG. 6 is a plan side view of an alternate embodiment of an anchoring system of the present invention.

FIGS. 5 and 6 depict an alternate embodiment in which base 22 is a non-continuous sheet of material and specifically is comprised from a series of individual mounting tabs 42. Lead lumen 23, however, abruptly bends towards bottom 31 of body member 13.

Figure 7:
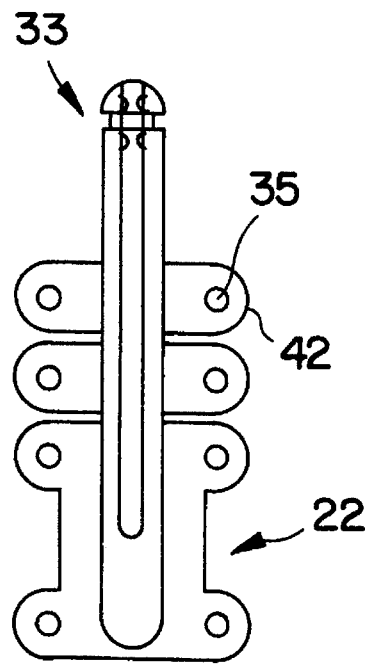
FIG. 7 is a plan top view of a further alternate embodiment of an anchoring system of the present invention.
Figure 8:
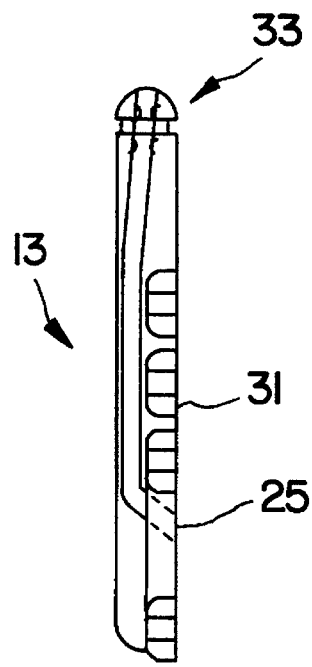
FIG. 8 is a plan side view of a further alternate embodiment of an anchoring system of the present invention.

FIGS. 7 and 8 depict an alternate embodiment in which base 22 is a composite of the previously discussed embodiments, specifically in which base 22 is a partial continuous sheet of material as well as a series of individual mounting tabs 42.

Figure 9:
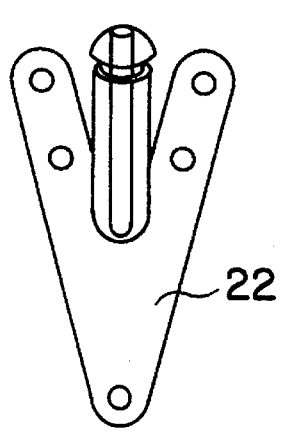
FIG. 9 is a plan top view of a further alternate embodiment of an anchoring system of the present invention.
Figure 10:
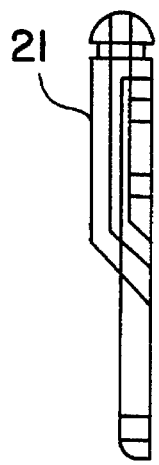
FIG. 10 is a plan side view of a further alternate embodiment of an anchoring system of the present invention.
Figure 11:
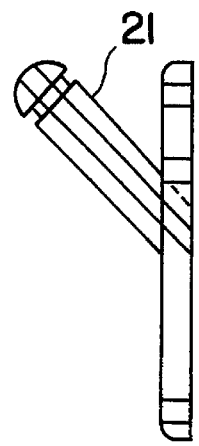
FIG. 11 is a plan side view of the alternate embodiment shown in FIG. 10 moved to a raised position.

FIGS. 9–11 depict an alternate embodiment featuring a triangular base 22 and a movable sleeve 21. Sleeve 21 specifically may be moved from its natural position, as depicted in FIG. 10, to its raised position, as depicted in FIG. 11. In such a manner lead lumen 23 may be transformed from the bent configuration show in FIG. 10, to the substantially straight configuration, shown in FIG. 11. Specifically lead lumen 23 is movable from a substantially parallel relation to base 22, wherein lead lumen 23 has a curve, to a substantially parallel relation to a foramen 4, wherein lead lumen 23 is straight. While in this configuration lead 12 may be readily inserted and positioned through body member 13. Once lead 12 has been properly positioned, sleeve 21 is allowed to fold back to its natural position as seen in FIG. 10 to thereby assist in securing lead 12 in position. As can be appreciated, the fact that the anchoring system provides a lead lumen substantially parallel to the base member, as opposed to upstanding, along with the pliant construction, provides strain relief to the lead therethrough so that any bending forces will not be concentrated in the area proximate the anchoring system.

Figure 12:
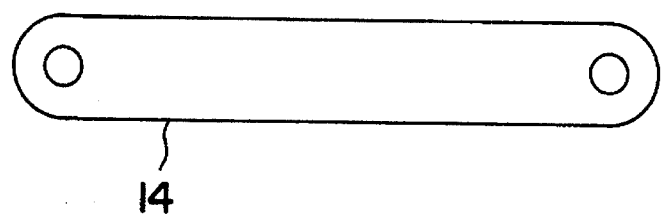
FIG. 12 is a plan top view of an elongate washer used in the present invention.
Figure 13:
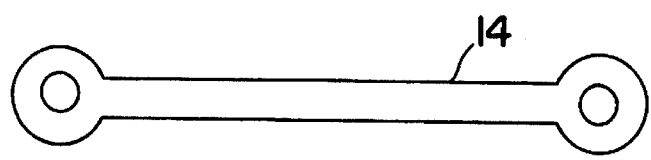
FIG. 13 is a plan top view of an alternate embodiment of an elongate washer used in the present invention.

Elongate washer 14 is depicted in FIGS. 12 and 13. Elongate washer 14 is preferably constructed from a biocompatible metal such as titanium. Screws 15 are also preferably constructed from a biocompatible metal such as titanium and designed to be fixed into bone. As seen in FIG. 13 elongate washer 14 may be shaped as an elongate dog-bone shaped washer.

Use of the anchoring system is as follows: Once the sacrum 2 and desired foramina 4 are uncovered, anchor body member 13 is inserted over lead 12. Body member 13 is positioned over foramina 4 and screw holes 43 are drilled therethrough, as seen in FIG. 2. Next lead 12, and specifically electrode at its distal tip (not shown) is inserted in foramina 4 and properly positioned to the appropriate nerve. Anchor body member 13 is then slid down lead 12 and fixed, through screws 15, in place and as described above. If satisfactory electrode placement is confirmed, then a suture (not shown) is tied around suture groove 33 to securely fix lead 12 within anchoring system 5 and thus to sacrum 2. Otherwise the electrode is maneuvered by either pushing or pulling along the section of the lead outside the sacrum and sleeve 21 until its position is satisfactory, then secured with a suture around suture groove 33.

Alternatively, body member 13 may be fixed in place as described above. Lead 12 may then be slid therethrough and positioned. Once positioned satisfactorily, lead 12 may be secured with a suture around suture groove 33.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A system for anchoring a lead to the sacrum comprising:
   a base, said base having at least one mounting hole therethrough, said base having a lead hole therethrough;
   a sleeve mounted to said base, said sleeve having a lead lumen therethrough, said lead lumen corresponding with said lead hole through said base, said lead lumen having means for fixing said lead to said sleeve, said sleeve and lumen being substantially parallel to said base;
   at least one fastener to be introduced through said mounting hole into said sacrum and thereby anchor the lead; and
   a stress distribution member to distribute the stress exerted from said fastener on said base.

2. The system of claim 1 wherein said base and sleeve are constructed from a pliant material.

3. The system of claim 1 wherein said base includes a reinforcing member.

4. The system of claim 3 wherein said reinforcing member is a nylon mesh.

5. The system of claim 1 wherein said stress distribution member is an elongate dog-bone shaped washer.

6. The system of claim 1 wherein said means for fixing said lead to said sleeve comprises a plurality of suture tabs in said sleeve.

7. A system for anchoring a lead to bone comprising:
   a base, said base having at least one mounting hole therethrough;
   a sleeve mounted to said base, said sleeve having a lead lumen therethrough, said lead lumen having a plurality of suture tabs therein to attach said sleeve to said lead, said sleeve having means for moving from a substantially parallel relation to said base to a substantially parallel relation to a hole in said bone;
   at least one fastener to be introduced through said mounting hole into said bone and thereby anchor the lead; and
   a stress distribution member to distribute the stress exerted from said fastener on said base.

8. The system of claim 7 wherein said base and sleeve are constructed from a pliant material.

9. The system of claim 7 wherein said base includes a reinforcing member.

10. The system of claim 9 wherein said reinforcing member is a nylon mesh.

11. The system of claim 7 wherein said stress distribution member is an elongate dog-bone shaped washer.

12. A system for anchoring a lead to bone comprising:
    a base, said base having at least one mounting hole therethrough, said base constructed from a pliant material, said base further having a reinforcing member to prevent said base from tearing proximate said at least one mounting hole;
    a sleeve mounted to said base, said sleeve having a lead lumen therethrough, said lead lumen having a plurality of suture tabs therein to attach said sleeve to said lead, said sleeve having means for moving from a substantially parallel relation to said base, wherein said lead lumen has a curve, to a substantially parallel relation to a hole in said bone, wherein said lead lumen is straight;
    at least one fastener to be introduced through said mounting hole into said bone and thereby anchor the lead; and
    a stress distribution member to distribute the stress exerted from said fastener on said base.

13. The system of claim 12 wherein said reinforcing member is a nylon mesh.

14. A system for anchoring a lead to a bone comprising:
    a base having at least one mounting hole therethrough, the base having a lead hole therethrough, the base having a sleeve, the sleeve having a lead lumen therethrough, the lead lumen coaxial with the lead hole, the lead lumen having means for fixing a lead to the sleeve;
    a stress distribution member positioned on the base, the stress distribution member having a screw hole; and
    a mounting screw positioned in the screw hole and through the mounting hole.

15. The system of claim 14 wherein the sleeve and lumen are substantially parallel to the base.

16. The system of claim 14 wherein the base and sleeve are constructed from a pliant material.

17. The system of claim 14 wherein the base includes a reinforcing member.

18. The system of claim 17 wherein the reinforcing member is a nylon mesh.

19. The system of claim 14 wherein the stress distribution member is an elongate dog-bone shaped washer.

20. The system of claim 14 wherein the means for fixing the lead to the sleeve comprises a plurality of suture tabs in the sleeve.

21. A system for anchoring a lead to a bone comprising:
    a base having at least one mounting hole therethrough, the base having a lead hole therethrough, the base having a sleeve, the sleeve having a lead lumen therethrough, the lead lumen coaxial with the lead hole, the sleeve having means for moving from a substantially parallel relation to the base to a substantially non-parallel relation to the base;
    a stress distribution member positioned on the base, the stress distribution member having a screw hole; and
    a mounting screw positioned in the screw hole and through the mounting hole.

\* \* \* \* \*